United States Patent [19]

Hussenet et al.

[11] Patent Number: 5,648,537
[45] Date of Patent: Jul. 15, 1997

[54] PROCESS FOR THE SYNTHESIS OF SUBSTITUTED CARBODIIMIDES

[75] Inventors: Patricia Hussenet, Athis Mons; Philippe Le Goff, Strasbourg; Gérard Sennyey, Saint Aubin, all of France

[73] Assignee: Societe Nationale des Poudres et Explosifs, Paris Cedex, France

[21] Appl. No.: 584,944

[22] Filed: Jan. 16, 1996

[30] Foreign Application Priority Data

Jan. 24, 1995 [FR] France .................. 95 00748

[51] Int. Cl.$^6$ .................. C07C 267/00
[52] U.S. Cl. .................. 564/252
[58] Field of Search .................. 564/252

[56] References Cited

U.S. PATENT DOCUMENTS

| 3,301,895 | 1/1967 | Sayigh et al. | 564/252 |
| 4,263,221 | 4/1981 | Schnabel et al. | 564/252 |

FOREIGN PATENT DOCUMENTS 1275307  2/1962  France .

OTHER PUBLICATIONS

Tetrahedon, vol. 37, 1981, Oxford GB, pg. 233–284, M. Mikolajczyk "Recent developments in carbodiimide chemistry".

Chemische Berichte, vol. 91, 1958, Weinheim De, pp. 1992–1995, J. Macholdt–Erdniss "Eine enifache Darstellung aromatischer Guanidine".

Angewandte Chemie, vol. 72, No. 22, 1960, Eilingsfeld et al.

Journal of Organic Chemistry, vol.29, 1964, Easton US, pp. 2401–2404, H. Ulrich et al. "Syntheses and some reactions of allophanoyl chlocrides".

*Primary Examiner*—S. Mark Clardy
*Assistant Examiner*—Mary C. Cebulak
*Attorney, Agent, or Firm*—Bucknam and Archer

[57] ABSTRACT

The invention relates to a new process for the synthesis of a disubstituted carbodiimide, including a first stage of phosgenation of an N,N'-disubstituted urea in an organic solvent medium.

After this first stage ammonia is added to the reaction mixture without preliminary isolation of any intermediate compound.

The process is simple, relatively inexpensive and the yield is high.

Disubstituted carbodiimides are organic synthesis intermediates used especially in pharmaceutical chemistry as coupling agents in peptide synthesis.

10 Claims, No Drawings

PROCESS FOR THE SYNTHESIS OF SUBSTITUTED CARBODIIMIDES

The present invention relates to a new process for the synthesis of disubstituted carbodiimides from N,N'-disubstituted ureas. Disubstituted carbodiimides, in particular N,N'-dicyclohexylcarbodiimide (DCC) are useful especially as synthesis intermediates in organic chemistry, for example in pharmaceutical chemistry as coupling agents, especially in peptide synthesis. During the coupling stages disubstituted carbodiimides are converted into the corresponding N,N'-disubstituted ureas. The process according to the invention is therefore particularly advantageous since it allows a byproduct to be recycled as raw material.

It is known to obtain disubstituted carbodiimides by reaction of a halogenating agent with an N,N'-disubstituted urea in an organic solvent medium.

According to Chemical Abstracts 95 (9): 80095j, Palomo and Mestres obtained disubstituted carbodiimides by reaction of N,N'-disubstituted ureas with $(C_6H_5)_3PBr_2$ in the presence of triethylamine and in $CH_2Cl_2$ medium. The yield was 90%.

According to Chemical Abstracts 105 (9):78567w and Chemical Abstracts 104 (9): 68491g, Haruta, Suematsu and Nakaoka obtained DCC by reaction of N,N'-dicyclohexylurea (DCU) with $POCl_3$ in the presence of pyridine. The yields were 79–80%.

These processes exhibit the disadvantage of giving rise to phosphorus-containing wastes and effluents, which is very costly on an industrial scale because of the need for treating these wastes and effluents.

In addition, the yields are not very high (approximately 80 to 90%) and the crude carbodiimide obtained after evaporation of the solvent must be purified by distillation.

It is known to employ phosgene as chlorinating agent for urea in order to be free from the phosphorus-containing wastes and effluents.

Japanese Patent JP 54076559 describes the preparation of DCC in 2 stages by phosgenation of DCU.

In a first stage the authors obtain and isolate from the reaction mixture N,N'-dicyclohexylchloroformamidinium chloride (DCFC) obtained by phosgenation of DCU in a dialkyl ether medium. This DCFC intermediate is then treated, in a second stage, with an aqueous solution of sodium hydroxide in the presence of dichloromethane, which enables DCC to be obtained. The overall yield of preparation of DCC from DCU is between 82% and 88%.

This two-stage process is long, costly and its yield is lower than 90%. It requires the isolation, by filtration and drying, of the intermediate compound DCFC, which is particularly sensitive to hydrolysis and therefore tricky to handle. It requires two reactors, two different solvents and, if the effluents and wastes do not contain any phosphorus, their quantity is large as a result.

The abovementioned processes are therefore not satisfactory, especially on an industrial scale, and a person skilled in the art is looking for a process which is simple to implement, inexpensive and which provides higher yields than those obtained hitherto, and which is ecological, that is to say giving rise to a small quantity of effluents and wastes which are devoid of toxic compounds.

The present invention proposes such a process and therefore a solution to the abovementioned problems.

Its subject-matter is a simple and relatively inexpensive process for obtaining a disubstituted carbodiimide, including a first stage of reaction of phosgene with an N,N'-disubstituted urea in an organic solvent medium.

It is characterized in that, after this first reaction stage of phosgenation of the N,N'-disubstituted urea, without preliminary isolation of the intermediate compound and especially of the chloroformamidinium chloride formed during this first stage, ammonia is added to the reaction mixture.

This method of operation is particularly advantageous on an industrial scale because of its simplicity and its low cost. The process is carried out in a single reactor, requires only a single solvent, and ammonia is a cheap reactant. The effluents and wastes are slightly toxic, if at all, and small in quantity.

This process also makes it possible, unexpectedly, to obtain, on the one hand, excellent yields, higher than 95%, even sometimes higher than 98%, and, on the other hand, a very pure, approximately 99%, synthetic crude carbodiimide which does not require special purification.

Such a result is particularly surprising for a number of reasons.

First of all, as shown by the comparative examples mentioned in the present application, this result is not obtained when, instead of ammonia, pyridine or a tertiary amine is employed, these being nitrogenous bases employed hitherto in combination with the chlorinating agent, as according to the abovementioned state of the art. This result does not therefore arise merely from the simplification of the process (a single reactor, a single solvent, no isolation of the intermediate derivative), but from a synergism between this simplification and the choice of a particular base, ammonia.

Furthermore, this result is all the more surprising since it was known to a person skilled in the art that ammonia, primary amines and secondary amines react with carbodiimides to form the corresponding guanidines. Reference may be made, for example, to Mikolajczyk and Kielbasinski, Tetrahedron, Vol. 37, Recent developments in the carbodiimide chemistry, page 245, and to J. Macholdt-Erdniss, Chemische Berichte, Vol. 91, 1958, Eine einfache Darstellung aromatischer Guanidine [A simple preparation of aromatic guanidines], page 1992.

It is furthermore quite certainly the reason for which, until then, the person skilled in the art only employed pyridine or tertiary amines as nitrogenous bases in order to obtain carbodiimides from ureas.

In addition, it was also known that primary amines react with the chloroformamidinium chloride intermediate to form guanidines. Reference may be made, for example, to Eilingsfeld, Seefelder and Weidinger, Angew. Chem. 72, 1960, No. 22, Amidchlorideund Carbamidchloride [Amide chlorides and carbamide chlorides], page 845.

For all these reasons the person skilled in the art was therefore very strongly dissuaded, in general, from employing ammonia for converting a chloroformamidinium chloride to the corresponding carbodiimide. This was all the more so since his objective was especially to markedly improve the yields obtained hitherto according to the known processes.

The Applicant Company is not in a position to put forward any explanation that could, even retrospectively, account for the results found.

The process according to the present invention is carried out in an organic solvent medium. The term "solvent" must not be taken in a restrictive sense. It should be understood that an organic medium which is unreactive in the operating conditions, commonly called an organic "solvent", is employed. According to the nature of the starting urea and of the organic "solvent", the urea may be in suspension and/or in solution in the organic solvent.

In order to carry out the present invention, each nitrogen atom of the urea must carry a hydrogen atom, that is to say that the "N,N'-disubstituted" terminology describing the urea must be understood in a restrictive sense, excluding the urea from being N,N'-tri- or tetra-substituted.

According to the present invention the N,N'-disubstituted urea preferably corresponds to the following general formula (I):

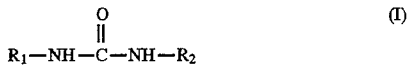

in which $R_1$ and $R_2$, which are identical or different, preferably identical, denote:

- a phenyl group which is unsubstituted or substituted, preferably by a halogen atom or an alkyl chain, for example $C_1$-$C_4$,
- a preferably $C_1$-$C_8$, better still $C_1$-$C_4$, linear or branched alkyl chain which is unsubstituted or substituted, for example by a halogen atom,
- a preferably $C_5$-$C_6$ cycloalkyl chain which is unsubstituted or substituted by a halogen atom or an alkyl chain, for example $C_1$-$C_4$.

Examples of particularly preferred ureas which may be mentioned are N,N'-diisopropylurea and N,N'-dicyclohexylurea.

When the urea corresponds to the general formula (I) the process according to the invention makes it possible to obtain a disubstituted carbodiimide of the general formula (II) according to the following reaction scheme, through the intermediacy of a chloroformamidinium chloride of the general formula (III):

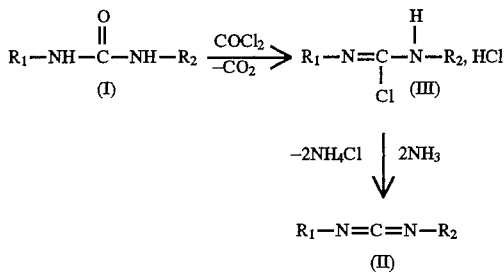

According to the invention the disubstituted carbodiimide obtained may be isolated from the reaction mixture by any means known to a person skilled in the art.

According to a first alternative form, for example, it is possible to filter the reaction mixture (the residue collected on the filter is essentially ammonium chloride), to collect the filtrate and then to strip the solvent, preferably by evaporation at reduced pressure.

It is found that this alternative form makes it possible to obtain a very pure synthetic crude carbodiimide requiring no special purification, according to a process carried out without any use of water.

According to a second alternative form it is also possible to performance aqueous extraction of the reaction mixture, the essential aim of which is to extract the ammonium chloride formed, followed by an evaporation of the organic solvent, for example at reduced pressure.

A very pure synthetic crude carbodiimide requiring no special purification, for example distillation, is also obtained according to this alternative form.

According to the invention the first stage of phosgenation of the N,N'-disubstituted urea in order to form the chloroformamidinium chloride includes a first operation of introducing phosgene into a suspension or a solution of the urea in the organic solvent, followed by a second operation of degassing of the reaction mixture using an inert gas, for example nitrogen or argon, or at reduced pressure. When the urea is poorly soluble in the solvent, the urea may be employed in suspension in the saturated solution.

The operation is preferably carried out in the presence of a slight excess of phosgene, that is to say more precisely that the molar ratio of phosgene to the urea is between 1.1 and 1.5.

Although any organic solvent may be suitable for making use of the process according to the invention, especially chlorinated solvents like $CHCl_3$ or $CH_2Cl_2$ and tetrahydrofuran (THF), it is preferred to employ an ether derivative, especially a dialkyl ether.

Examples of preferred dialkyl ethers which may be mentioned are those in which the alkyl chains contain from 1 to 5 carbon atoms, like, for example, diethyl ether, diisopropyl ether, diisobutyl ether, methyl butyl ether, methyl isopropyl ether and methyl tert-butyl ether. The latter is particularly preferred.

Preferably, on the one hand, the phosgene introduction period is longer than 3 h and, on the other hand, the temperature of the reaction mixture is between approximately 15° C. and approximately 25° C.

Furthermore, during the degassing operation, the temperature of the reaction mixture is preferably between b.p. $-3°$ C. and b.p. $-10°$ C., b.p. being the boiling temperature of the organic solvent, in degrees Celsius, at normal atmospheric pressure (101325 Pa, that is 760 mmHg), without, however, exceeding 70° C.

According to the invention, after the above-mentioned degassing operation, ammonia, preferably in the gaseous state, is introduced into the reaction mixture, without preliminary isolation of the intermediate compound and without any treatment of the reaction mixture other than an optional thermal treatment to lower its temperature.

During the introduction of the ammonia the temperature of the reaction mixture is preferably between $-5°$ C. and 10° C., still better between 0° C. and 8° C.

A slight excess of ammonia relative to the stoichiometry is preferably employed, which means that the molar ratio of ammonia to the N,N'-disubstituted urea is between 2 and 3.

The following nonlimiting examples illustrate the invention and the advantages which it provides.

EXAMPLE 1

Synthesis of DCC According to the Invention with Removal of Ammonium Chloride by Filtration 740 g (11) of methyl tert-butyl ether (MTBE) and 228.3 g of DCU are introduced, at ambient temperature and under nitrogen purging, into a 2-1 jacketed reactor fitted with mechanical stirring, a thermometer probe, a gas entry tube and a solid $CO_2$ condenser supporting a gas escape system. A suspension is obtained into which 131 g of phosgene are introduced continuously, with vigorous stirring, while the temperature of the reaction mixture is maintained between 15° C. and 20° C. The phosgene introduction period is 3.5 h.

After the introduction of phosgene the temperature of the reaction mixture is raised to 50° C. and the mixture is then degassed for 1 h by bubbling nitrogen through.

The temperature of the reaction mixture is then lowered to 2° C.

43 g of gaseous ammonia are then introduced into the mixture by bubbling, while its temperature is kept lower than 6° C.

After the introduction of ammonia, and then after the temperature of the mixture has been allowed to return to the ambient temperature (approximately 20° C.), the mixture is filtered to recover the filtrate. The filtration residue (essentially the ammonium chloride formed during the reaction) is washed on the filter with 3 times 300 ml of MTBE and the filtrates are then combined.

The solvent is then evaporated at reduced pressure (15 mmHg, that is approximately 2000 Pa), which makes it possible to obtain 207 g of a slightly coloured oil which solidifies at ambient temperature. The IR spectrum of this product agrees with the reference spectrum of DCC. Its purity, determined by gas phase chromatography, is 98.5%. The yield, based on the starting DCU, is 98.7%.

EXAMPLE 2

Synthesis of DCC According to the Invention with Removal of Ammonium Chloride by Aqueous Extraction In the case of this Example 2 the procedure followed is exactly as according to Example 1 until the end of the introduction of ammonia, except that 122 g of phosgene are introduced during 3.25 h instead of 131 g during 3.5 h and that 45 g of ammonia are introduced instead of 43 g.

After the introduction of ammonia and after the temperature of the mixture has been allowed to return to the ambient temperature, 400 g of water are added and stirring is then continued for 1 h.

After separation, the organic phase is recovered and this operation of aqueous extraction of the ammonium chloride formed is then repeated 3 times more, each time with 200 g of water and for 20 min.

After the last separation the organic phase is dried over magnesium sulphate and then the solvent is evaporated off at reduced pressure (approximately 2000 Pa), which makes it possible to obtain 200 g of a slightly coloured oil which solidifies at ambient temperature. The IR and $^1$H and $^{13}$C NMR spectra agree with the reference spectra of DCC. The purity of the DCC obtained, determined by gas phase chromatography, is 99.5%.

The yield, based on the starting DCU, is 95.3%.

Comparative Examples A and B

These 2 comparative examples do not form part of the invention. They were carried out with the sole aim of showing that the choice of ammonia as base for converting the chloroformamidinium chloride to carbodiimide is not arbitrary, but necessary to obtain the technical effect found and the results which stem therefrom (very high yields).

In the case of these Examples A and B the operation was carried out in a manner which was strictly identical with that described for Example 2, except that, instead of ammonia, 200 g of pyridine, added dropwise, were employed in Example A and 250 g of triethylamine, added dropwise, in Example B.

The DCC yield obtained, based on the starting DCU, was 66% in Example A and 80 % in Example B.

It is found, therefore, that these yields are very markedly lower than that obtained in Example 2, and that they are close to, or even slightly lower than, those obtained according to the abovementioned processes for obtaining DCC from DCU in the state of the art.

We claim:

1. Process for the synthesis of a disubstituted carbodiimide including a first stage of phosgenation of an N,N'-disubstituted urea in an organic solvent medium, characterized in that, after this first reaction stage ammonia is added to the reaction mixture without preliminary isolation of any intermediate compound.

2. Process of synthesis according to claim 1, characterized in that the N,N'-disubstituted urea corresponds to the general formula (I):

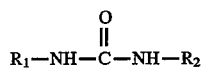

in which $R_1$ and $R_2$, which are identical or different, denote:

a substituted or unsubstituted phenyl group, a substituted or unsubstituted $C_1$-$C_8$ alkyl chain, a substituted or unsubstituted $C_5$-$C_6$ cycloalkyl chain.

3. Process of synthesis according to claim 1, characterized in that the N,N'-disubstituted urea is N,N'-dicyclohexylurea.

4. Process of synthesis according to claim 1, characterized in that, after the addition of ammonia, the carbodiimide formed is isolated by filtration or aqueous extraction of the reaction mixture, followed by an evaporation of the organic solvent.

5. Process of synthesis according to claim 1, characterized in that the first stage of phosgenation of the N,N'-disubstituted urea includes a first operation of introducing phosgene into a suspension or a solution of the urea in the organic solvent, followed by a second operation of degassing of the reaction mixture using an inert gas or at reduced pressure.

6. Process of synthesis according to claim 1, characterized in that the organic solvent is a dialkyl ether.

7. Process of synthesis according to claim 5, characterized in that the phosgene introduction period is longer than 3 h and in that during the introduction of phosgene the temperature of the reaction mixture is between approximately 15° C. and approximately 25° C.

8. Process of synthesis according to claim 5, characterized in that during the degassing operation the temperature of the reaction mixture is between b.p. −3° C. and b.p. −10° C., b.p. being the boiling temperature of the organic solvent, in °C., at normal pressure, without, however, exceeding 70° C.

9. Process of synthesis according to claim 1, characterized in that during the addition of ammonia the temperature of the reaction mixture is between −5° C. and 10° C.

10. Process of synthesis according to claim 1, characterized in that the molar ratio of phosgene to the N,N'-disubstituted urea is between 1.1 and 1.5 and in that the molar ratio of ammonia to the N,N'-disubstituted urea is between 2 and 3.

* * * * *